United States Patent [19]

Schulman

[11] 4,071,032

[45] Jan. 31, 1978

[54] IMPLANTABLE LIVING TISSUE STIMULATORS

[75] Inventor: Joseph H. Schulman, Los Angeles, Calif.

[73] Assignee: Pacesetter Systems Inc., Sylmar, Calif.

[21] Appl. No.: 653,462

[22] Filed: Jan. 29, 1976

[51] Int. Cl.$^2$ .............................................. A61N 1/36
[52] U.S. Cl. ................................................. 128/419 P
[58] Field of Search ............ 128/419 P, 419 PG, 421, 128/422, 423; 361/212, 220

[56] References Cited

U.S. PATENT DOCUMENTS

| 3,195,540 | 7/1965 | Waller | 128/419 PG |
| 3,357,434 | 12/1967 | Abell | 128/419 P |
| 3,547,127 | 12/1970 | Anderson | 128/419 PG |
| 3,888,260 | 6/1975 | Fischell | 128/419 PS |

OTHER PUBLICATIONS

Tyers et al., "Medical Instrumentation," vol. 8, No. 2, Mar.-Apr. 1974, pp. 178-179.

*Primary Examiner*—William E. Kamm

*Attorney, Agent, or Firm*—Lindenberg, Freilich, Wasserman, Rosen & Fernandez

[57] ABSTRACT

An implantable living tissue stimulator is described with a current conductive protective shield, to prevent the flow of currents to or from the stimulator circuitry via the electrically conductive body fluid. Also disclosed is an implantable living tissue stimulator of the rechargeable type in which the stimulator circuit components are surrounded by a pickup coil, designed to pick up an external magnetic field for recharging the power source, e.g., battery of the stimulator. One embodiment incorporates one or more ferrite slabs extending through the coil wound about the rest of the stimulator components, in order to increase the coil pick up efficiency and to divert the magnetic field from the stimulator metal components, such as a metal container in which the stimulator circuitry is hermetically sealed and thereby minimize the heating of the components and/or metal container. Also disclosed is a stimulator in which the coil, wound about the stimulator circuit components and the ferrite slabs, is sealed within a ceramic or glass hermetic container which is impervious to body saline fluid or gases.

25 Claims, 11 Drawing Figures

IMPLANTABLE LIVING TISSUE STIMULATORS

BACKGROUND OF THE INVENTION

1. Field of the Invention:

The present invention generally relates to living tissue stimulators and, more particularly, to new improved implantable living tissue stimulators.

2. Description of the Prior Art:

Various devices are presently in existence which are implantable in a living body in order to stimulate selected body tissues. Among the best known living tissue stimulators is the cardiac pacemaker, which provides stimulating pulses to a patient's heart via one or more electrodes connected to the pacemaker through electrode leads. Some commercially available implantable pacemakers consist of pulse generating circuitry and a proper power source which are encapsulated in resinous material, e.g., epoxy, which is intended to serve as electrical insulation and as a body fluid impervious barrier. As is appreciated, the body fluid is a saline solution which is electrically conductive.

From experience with such pacemakers it has been discovered that even though the encapsulating material is intended to serve as an impervious barrier to the body fluid it is not a very good barrier. The body fluid tends to impregnate the encapsulating material, particularly through small cracks therein. Such impregnation presents a significant danger to the patient. The danger is due to the fact that currents from the power source and/or from the pulse generating circuitry may flow out of the pacemaker through the impregnating body fluid to the rest of the body. Such currents may damage body tissue, thereby endangering the patient. The danger of current flow from the pacemaker to the rest of the body is particularly significant in a pacemaker whose power source is rechargeable by means of an external magnetic field, due to the presence of significant voltage and currents during recharge.

In addition, it is highly desirable to protect the pacemaker circuitry from any currents from external sources which may flow to the circuitry through the impregnating body fluid, thereby potentially affecting the proper operation of the pacemaker circuitry. Thus, a need exists for means for use with an implantable pacemaker to inhibit the flow of current through the body fluid (except to the electrodes through their leads) either out of the pacemaker to the rest of the body or into the pacemaker from an external source.

Also, in any implantable pacemaker it is highly desirable to protect the stimulator circuit components from adverse effects due to an external alternating magnetic field, which may interfere with the proper operation of the stimulator circuitry as well as heat up its components. Such protection is of particular importance in an implantable rechargeable pacemaker which includes a pickup coil in which current is induced by an external alternating magnetic field to recharge a power source. e.g., a battery. At present an implantable rechargeable pacemaker is available in which all the circuit components are hermetically sealed in a hermetic metal container. In such a pacemaker, a significant portion of the power induced by the external alternating magnetic field is dissipated as heat in the metal container and metal circuit components. The portion of the total induced power which is converted into useful battery charging power is small. Thus, a need exists for an improved implantable rechargeable hermetically sealed pacemaker.

OBJECTS AND SUMMARY OF THE INVENTION

It is a primary object of the present invention to provide an improved implantable living tissue stimulator.

Another object of the invention is to provide a novel implantable living tissue stimulator with means for inhibiting the flow of undesired currents from the stimulator to the rest of the body.

A further object of the invention is to provide an implantable living tissue stimulator with means which protect the stimulator circuitry from currents from external sources, conductable thereto via the body fluid, said means further protecting body tissue from the flow of undesirable currents from the pacemaker circuitry.

Yet another object of the present invention is to provide an improved implantable rechargeable living tissue stimulator.

Yet a further object of the invention is to provide improvements in an implantable living tissue stimulator of the type including a coil in which a current is induced either by an external alternating magnetic signal, or by stimulator circuitry.

Still a further object of the present invention is to provide an improved implantable rechargeable hermetically sealed living tissue stimulator.

These and other objects of the invention are achieved by providing an implantable living tissue stimulator in which all circuit elements, which may come in contact with body fluid, are surrounded by an electrically conductive protective shield, which is connected to a point or line which is at a common reference voltage of the pacemaker circuitry, hereinafter referred to as the system common point. As a result, any current flowing out of the stimulator circuitry, via the body fluid, is conducted by the shield back to the system common point and is thereby prevented from flowing toward any body tissue which may be damaged by such current. Similarly, any current from an external source which may flow toward the stimulator, via the body fluid, is bypassed (shunted) around the circuitry by the shield.

Also provided is a stimulator in which a coil, in which a current is assumed to be induced by an external alternating magnetic field, is wound about the stimulator circuitry and one or more slabs of high magnetic permeability material, e.g., ferrite, in order to increase the magnetic field passing through the coil and reduce the heating of the circuitry or interference with its normal operation, due to the external magnetic field. The coil may also be one in which a current is induced by the stimulator circuitry in order to transmit a signal to outside the body in which the stimulator is implanted. The coil may be a pickup coil which forms part of a recharging circuit, designed to recharge the stimulator power source, e.g., a battery. The stimulator with the coil wound about the stimulator circuitry and the high magnetic permeability material may be hermetically sealed within a hermetic container formed of glass and/or ceramic, which is impervious to body fluid or gases.

The novel features of the invention are set forth with particularity in the appended claims. The invention will best be understood from the following description when read in conjunction with the accompanying drawings.

DESCRIPTION OF THE PREFERRED EMBODIMENTS

The disadvantages of prior art living tissue stimulators and the advantages provided by the present invention will be described in connection with a cardiac pacemaker. From the following description it will become clear that the invention is not intended to be limited to a cardiac pacemaker only and is applicable for use with or forming part of any implantable living tissue stimulator.

Figure 1:
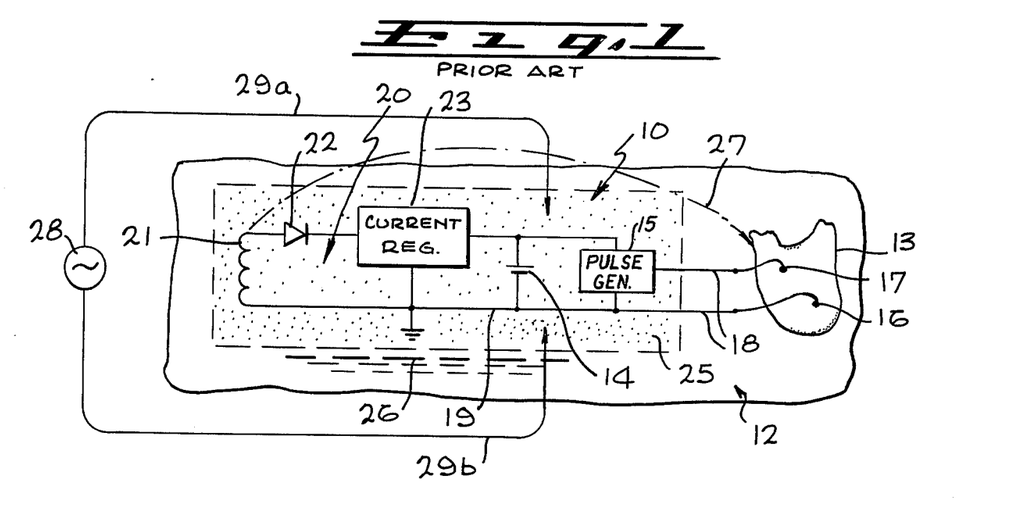
FIG. 1 is a simplified cross-sectional and block diagram of a prior art stimulator.

FIG. 1 to which attention is directed is a simplified diagram of a pacemaker 10 of the rechargeable type, which is shown implanted in a living body represented by 12, that requires stimulation of the heart 13. The pacemaker 10 typically includes a power source, e.g., a battery 14, which powers a pulse generating circuit 15 to energize electrodes 16 and 17 which extend into the heart 13 via electrode leads 18. The pacemaker circuitry includes a line, such as line 19, which is at a common reference potential or voltage of the system, represented in FIG. 1 as ground. Typically, one of the electrodes, such as electrode 16, is connected to this line, referred to as the system common point. The pulses generated by pulse generating circuitry 15 are impressed across electrodes 16 and 17.

The pacemaker 10 shown in FIG. 1 is assumed to include a recharging circuit 20, used to recharge the battery 14. The circuit 20 includes a pickup coil 21 in which high currents are induced by an alternating magnetic field, provided external to the body 12. The currents induced in the coil 21 are rectified by a rectifier, represented for explanatory purposes by the single diode 22. The rectified current is then regulated by a current regulator 23 and is used to recharge the battery 14.

Typically, the pacemaker system, i.e., the recharging circuit 20, the battery 14 and the pulse generating circuitry 15, hereinafter referred to as the pacemaker system components or circuitry, are encapsulated in electrically insulating implantable grade encapsulating material 25. Many different materials, including epoxy, which can be used as the encapsulating material 25 are well known. To simplify the following description the encapsulating material 25 will be referred to as epoxy 25. The function of the epoxy 25 is to provide mechanical support and electrical insulation for the pacemaker circuitry as well as to serve as an impervious barrier to the electrically conductive body fluid 26, which surrounds the pacemaker 10 when the latter is implanted in the body 12. In U.S. Pat. No. 3,735,766 a pacemaker which can be operated as either a unipolar type or a bipolar type is disclosed, while in U.S. Pat. No. 3,867,950 a fixed rate cardiac pacemaker of the rechargeable type is disclosed.

Although the epoxy 25 is intended to act as an impervious barrier to body fluid 26 in practice this is not the case. With the passage of time the body fluid tends to penetrate or impregnate the epoxy 25. This is most undesirable since the body fluid is electrically conductive, the body fluid is capable of providing current conductive paths for leakage currents from the pacemaker internal components to the outside of the pacemaker. Such leakage currents may present serious danger to the patient. For example, any current leaking from the high voltage end of the coil 21, represented by numeral 27 may be conducted via the body fluid 26, through the external wall of the heart 13 and therefrom through electrode 16 to the system common point back to the common point side of coil 21. As a result, the high current flowing in the coil 21 is impressed directly across the heart wall which may be damaging to the patient. Also, any leakage of currents from any other components of the pacemaker to body tissues may damage or destroy such body tissues which is of course most undesirable.

In addition, quite often external currents from a generator outside the body, such as generator 28 may flow via the body fluid through paths indicated by 29a and 29b in the vicinity of the pacemaker. Such external currents unless prevented from reaching the pacemaker circuitry may seriously affect the pacemaker proper operation. Thus, it is obvious that it is necessary to protect the pacemaker from the flow of currents from it and to it via the body fluid in order to protect body tissue from dangerous currents flowing out of the pacemaker as well as to protect the pacemaker circuitry from malfunctioning due to external currents flowing through it.

The present invention solves the problem of the conduction of undesired current from the pacemaker 10 to the rest of the body via the body fluid 26, as well as the conduction of external currents through the pacemaker by surrounding the pacemaker with a current conductive protective shield. The shield is connected electrically to the system common point such as line 19. The shield is formed of low or non-magnetic electrically conductive material, such as a low or non-magnetic metal. Since the shield will come in contact with body fluid it should be formed from a metal which exhibits reasonably high biocompatible properties. Its electrical conductivity is higher than that of the body fluid. Consequently, any current which flows out of the pacemaker via the body fluid upon reaching the shield is conducted back to the pacemaker system common point by the shield. Similarly, any external current flowing in the vicinity of the pacemaker, upon reaching the shield is conducted around the pacemaker via the shield rather than through the pacemaker pulse generating circuitry, which may be adversely affected by such an external current. Some examples of metals which are generally regarded as biocompatible and which can be used to form the shield include stainless steel, titanium, titanium alloys, cobalt-chromium alloys, niobium, tantalum and zirconium.

Figure 2:
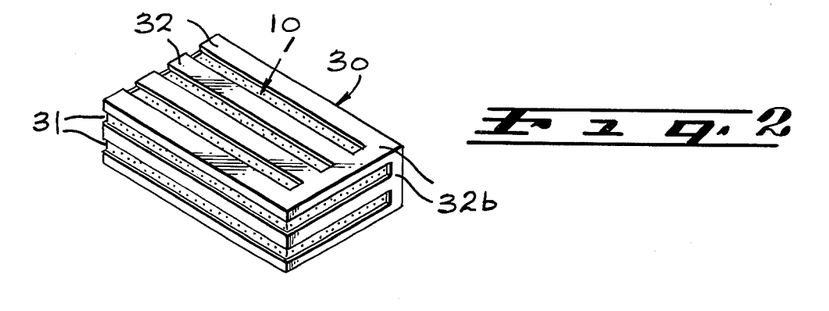
FIGS. 2 and 3 are diagrams of one embodiment of a conductive current protective shield in accordance with the present invention.

Attention is now directed to FIG. 2 which is a simplified isometric view of one embodiment of a current conductive protective shield 30 which is assumed to completely surround a conventional pacemaker such as pacemaker 10, which is not hermetically sealed, i.e., one in which the pacemaker internal components are encapsulated in epoxy 25 but one not surrounded by a hermetically sealing metal container or can. The shield 30 which surrounds the entire pacemaker 10 forms a metal enclosure around the pacemaker 10, which is assumed to be box-shaped. However, rather than being a closed metal can the shield 30 is slotted by slots 31 which effectively divide the shield into a plurality of separate electrically conductive strips 32.

Figure 3:
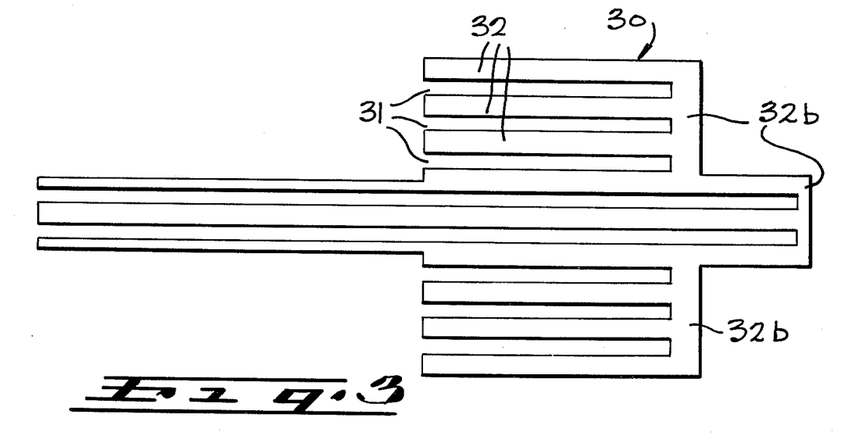

A planar view of the shield 30 before it is folded to surround the pacemaker 10 about its six sides is shown in FIG. 3. As seen, the conductive strips 32 are spaced apart from one another. However, they are all electrically connected at one narrow region of the shield 30 designated in FIGS. 2 and 3 by 32b. It is this region which is electrically connected to the system common point against which current flow is to be protected, such as common line 19 in FIG. 1. However, except for this region the strips are electrically separated from one another, so that no electrically conductive path is produced between any two strips 32. With such a shield construction, the heat generated in any substantially square area on any strip surface through which the external alternating magnetic field passes can be kept small by making the strips' widths small so that the maximum square areas are small. Thus, the heat generated due to the alternating magnetic field passing through the small square areas on the strips' surfaces is held to a minimum, as compared with the heat which would have been generated in the shield 30 in the absence of the slots 31. The slots may be made quite wide so as to reduce the total shield weight. However, they have to be sufficiently narrow to insure that any undesired current flowing from or to the pacemaker does not pass through any of the slots, but rather is shunted to the adjacent strips 32.

From the foregoing it should be appreciated that by providing the shield 30 around the non-hermetically sealed pacemaker, undesired currents from the pacemaker are prevented from flowing beyond the shield 30, thus preventing potential damage to body tissue from such currents. Also, the flow of undesired external currents through the pacemaker internal components is bypassed by the shield which effectively shunts such currents around the internal pacemaker circuits which need to be protected from such external currents.

Although the embodiment of shield 30 as shown in FIGS. 2 and 3 is believed to be a preferred one, the invention is not intended to be limited thereto. The shield may be formed by spaced-apart electrically conductive wires which are spaced apart from one another, except that they are all electrically connected only at one junction, which is in turn connected to the system common point against which current flow is to be protected. The wires which should be in direct electrical contact with the body fluid should not be interconnected so as to produce relatively large closed loops of wire. This is necessary to prevent the generation of heat in the large closed loops. The spacing between wires should be small enough to provide sufficient current shunting to the wires in order to reduce current flow via the body fluid to or from the pacemaker in the spaces between the wires to below an acceptable desired level.

In general, the electrically conductive protective shield should be formed so that the maximum square areas on the strips' surfaces through which the alternating magnetic field passes are small, e.g., 0.2 square inch or less to prevent the generation of excessive heat in the shield. The spacing between conductive portions of the shield should be sufficiently small, e.g., 0.001 inch (1 mil) to insure that any leakage current generated within the pacemaker and conducted, via the body fluid, is shunted to the shield, which provides a current conductive path to the system common point to which the shield is connected. For example, in the circuitry shown in FIG. 1 of U.S. Pat. No. 3,867,950 the shield 30 may be connected to the lower end of the pickup coil 31. Also, leakage currents generated external to the pacemaker which may conduct via the body fluid toward the pacemaker are shunted by the shield around the pacemaker, thereby protecting its circuitry from such leakage currents.

The novel current conductive protective shield in accordance with the present invention is not intended to be limited to the embodiments hereinbefore described. For example, the shield may consist of electrically conductive fins extending outwardly from the pacemaker 10 with insulating material between the fins. Each fin should be connected to the system common point with no return path between the fins. If the fins' dimensions, extending outwardly from the pacemaker, are substantially greater than the spacings between adjacent fins any current attempting to flow to or from the pacemaker through the insulating material, which is impregnated by body fluid, will be shunted through the adjacent fins either around the pacemaker or to the system common point to which the fins are connected.

Figure 4A:
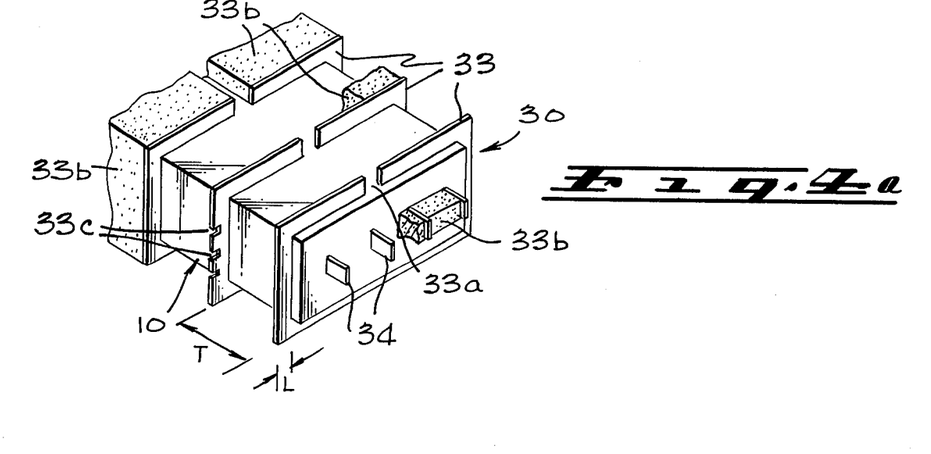
FIGS. 4a and 4b are diagrams of another embodiment of the protective shield.
Figure 4B:
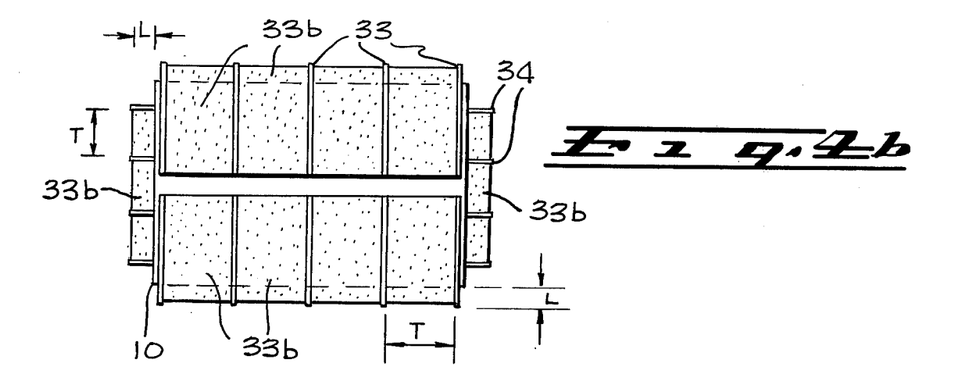

An example of such an embodiment of the shield 30 is diagrammed in FIGS. 4a and 4b. In these figures the pacemaker 10 is assumed to be in the shape of a six-sided box, with FIG. 4a being a partial isometric view of the pacemaker and the shield 30, while FIG. 4b is a top view of the shielded pacemaker. In FIG. 4a, numerals 33 designate spaced apart electrically conductive strips, each forming outwardly extending fins on four (front, top, back and bottom) sides of pacemaker 10. Each strip 33 should have a gap 33a to prevent the strip from forming a continuous closed conductive strip. The dimension of the strip extending outwardly is designated by L. The spacing between strips 33 is T and in practice is filled with electrically insulating material 33b. In practice, L is greater than T, although in FIG. 4a the reverse is shown for explanatory purposes only. If necessary, the strips 33 may be slotted with narrow inwardly directed slots 33c in order to reduce the heating of the strips by reducing the maximum sizes of substantially square areas on the fins' surfaces through which the alternating magnetic field can pass.

The other two sides of pacemaker 10 may be protected by one or more rows of spaced apart electrically conductive metal strips 34, which like strips 33 are spaced apart from one another, with the spaces between them filled with insulating material 33b. These strips 34 may also be slotted with slots 33c for the reasons hereinbefore explained. Also, for optimum shielding the lengths of strips 34 away from pacemaker 10 should be considerably greater than their spacings. In FIG. 4b the lengths of strips 34 and their spacings are also designated by L and T respectively. The ratio of L/T should be not less than 2 and preferably 10 or more. It should be stressed that each of the strips 33 and 34 should be connected to the system common point, and that no continuous return conductive path should be present between any of the strips.

At present a rechargeable hermetically sealed pacemaker is available commercially. It includes a container or a can of a biocompatible metal, such as a wroughtable cobalt-chromium alloy of a thickness on the order of about 10 mils. The metal can, which is impervious to body fluid, hermetically seals the recharging circuitry 20 including pickup coil 21, the battery 14 and the pulse generating circuitry 15. The electrode leads 18 extend out of the metal can through a hermetically sealing connector. Internally, the can is generally connected to the system common point. Consequently, the metal can acts as a current conductive protective shield which protects the flow of dangerous currents from the pacemaker as well as bypasses the flow of currents from external sources around the pacemaker circuitry.

The above-described rechargeable hermetically sealed pacemaker has been widely accepted and performs with a high degree of reliability. One basic disadvantage of this pacemaker is due to the fact that the pickup coil is located inside the metal can, and therefore its pickup efficiency is not sufficiently high. The external magnetic field has to pass through the metal can before passing through the coil so as to induce recharging currents therein. Since the metal can is of a continuous sheet of metal a substantial portion of the power which is induced in the pacemaker by the external alternating magnetic field is dissipated as heat in the metal can. This is very undesirable, since the heated can may cause patient discomfort and/or damage body tissue. Also, since a substantial portion of the induced power is dissipated as heat, only a very small portion thereof is available for conversion into useful battery recharging power.

Figure 5:
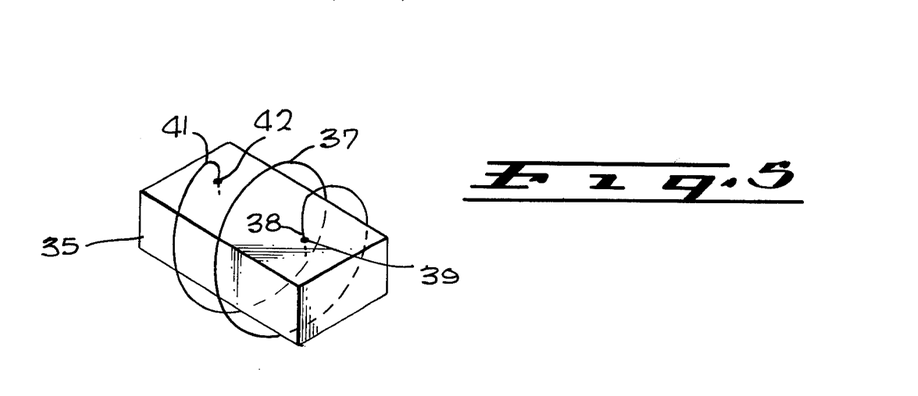
FIG. 5 is a diagram of a stimulator with a coil wound about the rest of the stimulator components.

It has been discovered that the pickup efficiency of the pickup coil can be increased significantly by winding the pickup coil outside of the metal can, such as around it, while all the other pacemaker components are hermetically sealed in the metal can. Such an arrangement is shown in FIG. 5, wherein numeral 35 designates the metal can which is assumed to hermetically seal all of the pacemaker components, except for the pickup coil. The latter which is formed with several turns or windings, is designated by 37 and is shown wound about the metal can 35. End 38 of coil 37 is assumed to extend into the can 35 through a hermetic seal 39, such as a glass or ceramic seal, while the opposite end 41 of the coil 37 is electrically connected to the can 35 at junction 42 on the outer can surface.

Figure 6:
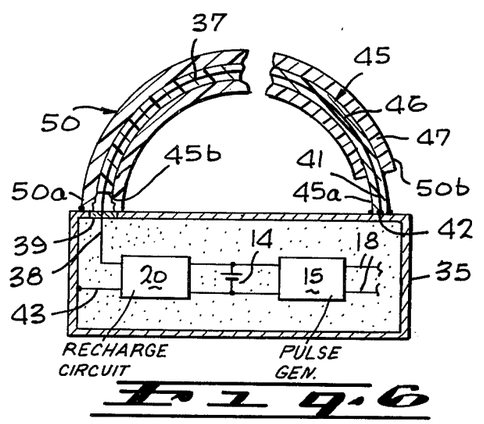
FIGS. 6, 6a and 6b are diagrams useful in explaining a two-coaxial shield for an externally wound coil.

As shown in FIG. 6, which is a simplified crosssectional view of this embodiment of the invention, the end 38 of coil 37, which extends through seal 39 into container 35, is connected to the charging circuitry 20, which is also connected by conductive wire 43 to the can 35. Thus, even though the coil 37 is wound external to the metal can 35 it is electrically connected to the rest of the recharging circuitry 20, which is hermetically sealed in can 35. In practice, the electrode leads 18 extend out of the can 35 through a hermetically sealing connector. However, since this feature does not form part of the invention, it is not shown in FIG. 6.

In practice, the coil 37 is covered by electrically insulating material. However, the latter, like the epoxy 25, is not impervious to body fluid. Thus, even though most of the pacemaker components are hermetically sealed in metal can 35, the coil is not. In use, unless the coil is protected, currents may flow therefrom and thereto via the body fluid, as previously explained in connection with the non-hermetically sealed pacemaker 10, described in connection with FIG. 1. Therefore, it is desirable to provide a current conductive protective shield for the externally wound coil 37.

One possible arrangement is to surround the coil 37 as well as the metal can 35, as shown in FIG. 5, with the shield 30. From the foregoing, it should be apparent that shield 30 would prevent the flow of current from the coil 37 beyond the shield 30 as well as the flow of external currents to the coil. Another arrangement of shielding the coil 37 is represented in cross sectional view in FIG. 6. Therein only portions of the coil 37 near its opposite ends are shown.

Basically, the coil 37 is surrounded by a circular conductor 45 which is insulated from the coil 37 by the insulation 46 surrounding it. One end, such as end 45a of conductor 45 is connected to the can 35, while its opposite end 45b is free-floating. In FIG. 6, the end 45a of conductor 45 is assumed to be connected to the can 35 around junction 42 at which the coil end 41 is connected to the can, while the conductor 45 free-floating end 45b extends up to near the opposite end 38 of the coil, which enters into the can 35 through seal 39. Surrounding the circular conductor 45 is an outer circular conductor 50, which is insulated from conductor 45 by the outer insulator 47. Conductor 50 has its end 50a connected to the metal can 35. The outer conductor extending from its end 50a surrounds the coil portion which is not shielded by inner conductor 45, and further extends around inner conductor 45 up to an opposite end 50b which, like end 45b of conductor 45, is free-floating. That is, it is not connected to either the coil, the other conductor or to the metal can 35.

It should first be pointed out that each of conductors 45 and 50 has only one end connected to the metal can 35, while its other end is free-floating. Thus, it does not form a continuous closed electrically conductive path, in order to prevent the external alternating magnetic field from generating heat in the conductor. Except for the short portion of coil 37 near end 41, which is not surrounded by conductor 50, any external current flowing to the coil, via the body fluid, will be shunted to the can by the outer conductor 50, thereby being prevented from reaching the coil. Near end 41 of coil 37 the flow of external current to the coil is prevented by the inner conductor 45 whose end 45a is connected to the metal can. Thus, the coil 37 is protected from the flow of external currents thereto. Similarly, the flow of currents from the coil 37 to any body tissue is prevented by the conductors 45 and 50. Over most of the coil length, except near end 38, the flow of any current from the coil 37 is conducted to the metal can by the inner conductor 45, and near end 38 by the outer conductor 50. On the other hand, the flow of current from the coil 37 near coil end 41 is shunted by the inner conductor 45, to the metal can which is assumed to be connected to the system common point.

Figure 6A:
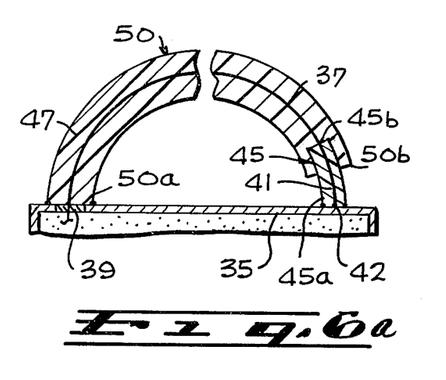
Figures 6B, 7, 8:
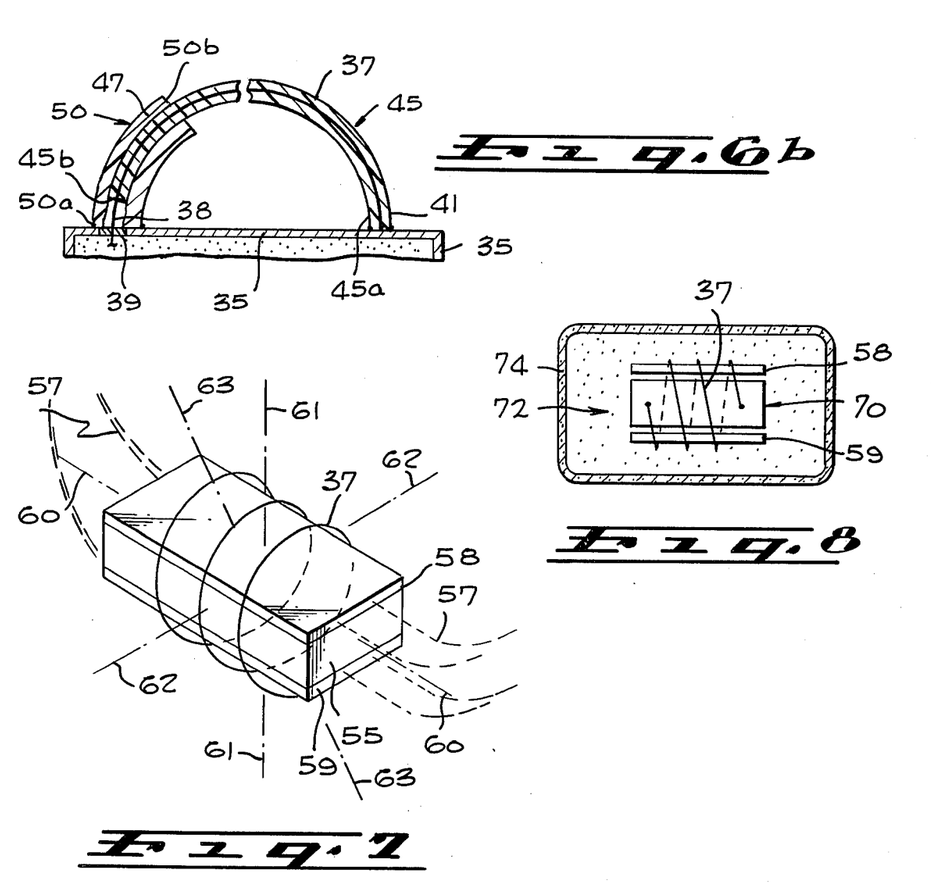
FIG. 7 is an isometric diagram of another embodiment of the invention.
FIG. 8 is a diagram of yet another embodiment of the invention.

In FIG. 6, each of the conductors 45 and 50 is shown surrounding most of the coil length, each extending from a different coil end up to near the opposite end of the coil. In practice, however, this is not an absolute requirement. If desired, the inner conductor 45 may extend only part way into the outer conductor from its free-floating end 50b, as shown in FIG. 6a. Also, outer conductor 50 need not extend all the way up to near end 41 of the coil 37. Its end 50b may terminate after overlapping a reasonable portion of the inner conductor 45 beyond its end 45a, as shown in FIG. 6b. It should be pointed out that each of conductors 45 and 50 need not be a continuous cylindrical conductor. Each may consist of one or more strips or wires which are helically wound, so as to form a current conductive shield around coil 37.

The two conductors 45 and 50 can be viewed as a two coaxial current conductive shielding arrangement around the coil 37 with opposite ends of the two conductors connected to the metal can to which one end of the coil is connected. The other ends of the two conductors are free-floating, with at least a portion of the coil 37 being surrounded by both conductors. For optimum performance it is desirable that the radius of the inner conductor 45, i.e., the distance between its inner surface and coil 37 be small compared with the length of conductor 45, to insure that any currents leaking out of the coil portion surrounded by conductor 45 reach the latter rather than pass through its free-floating end 45b. Also, the difference between the radii of the inner and outer conductors should be small compared with the length of coil over which the two conductors overlap. This is desirable to maximize the likelihood that any currents flowing in the insulation 47 are conducted to either of the conductors 45 and 50 and do not pass through the free-floating end 50b of outer conductor 50.

In general, the ratio between the radii different designated $T_1$ and the overlapping section designated $L_1$, i.e., $L_1/T_1$, should be not less than 2 and preferably 10 or more. If one were not concerned with leakage of very small currents to or from the coil near the end 41 which is connected to the can, the inner conductor 45 can be left out. In this case the free-floating end 50b of conductor 50 should be as close as possible to the coil end 41 which is connected to the can 35.

From the foregoing it should thus be appreciated that the two coaxial shielding arrangement protects the coil from conduction of currents via the body fluid to or from the coil, beyond the shielding arrangement, while the metal can 35 protects the rest of the pacemaker circuitry from such currents. Although the coil 37 has been assumed as the pickup coil for battery recharging the two coaxial shielding arrangement can be used to shield a coil, which may be used for any other purpose in a pacemaker, from current conducted thereto or therefrom via the body fluid. For example, in a pacemaker with a coil used to transmit alternating magnetic signals to the body exterior and/or receive alternating magnetic signals therefrom the two coaxial shielding arrangement may be used to shield such a transmit and/or receive coil.

Herebefore in the description of the embodiments shown in FIGS. 5 and 6 it was assumed that metal can 35 is a hermetically sealing container. This was presented for explanatory purposes only. In practice the metal can 35 need not hermetically seal the pacemaker components. It can be used as a shield to protect current flow from or to the pacemaker components. However, the slotted shield 30 shown in FIG. 3 is believed to be a preferred embodiment of such a shield for reasons hereinbefore discussed.

In the embodiment hereinbefore described in connection with FIGS. 5 and 6, the end 41 of coil 37 is assumed to be connected to the metal can 35, which is internally connected to the system common point against which current flow is to be protected. This arrangement is presented for explanatory purposes only. Clearly, if desired end 41 of coil 37 may extend into the can 35 through another hermetic seal, similar to seal 39, and be directly connected to circuitry 20, so that neither coil end is tied to the system common point. Also, if the metal can is not connected internally to the system common point, the ends 45a and 50a of the conductors 45 and 50, instead of being connected to the metal can, should extend therethrough and be connected to the system common point within the metal can 35.

The pickup efficiency of an alternating magnetic field by the externally wound coil 37 may further be increased significantly by inserting through the coil a ferrite core or slab. This important aspect of the invention may best be described in connection with FIG. 7. Therein, numeral 55 represents a metal can, which is assumed to hermetically seal the internal components of a pacemaker which include metal parts, except for the externally wound coil 37. For explanatory purposes, coil 37 is assumed to be a pickup coil, forming part of a battery recharging circuit. In FIG. 7 an externally applied alternating magnetic field which is designed to pass through coil 37 is represented by magnetic flux lines 57.

In accordance with the present invention, as shown in FIG. 7 a pair of ferrite slabs 58 and 59 are wrapped around by the coil 37. The slabs are shown located on opposite sides (top and bottom) of the metal can 55. These ferrite slabs perform two very important functions. The ferrite slabs due to their high magnetic permeability maximize the pickup efficiency of the coil 37. Also, they effectively shield the pacemaker metal parts, which include the metal can 55 and any metal parts therein, from the magnetic field by shunting the magnetic field around the pacemaker metal parts. Since most of the magnetic field effectively bypasses the metal parts of the pacemaker, little if any heating is induced in the pacemaker metal parts between the ferrite slabs, which is very advantageous.

In the present invention since the ferrite slabs divert the magnetic field from passing through the pacemaker metal parts, the production of a magnetic field by these parts which opposes field 57 does not occur. Thus, a stronger magnetic field passes through the coil 37 than would have been the case with metal present but without the ferrite slabs. Also, by using ferrite slabs which exhibit high electrical resistivity very little heating takes place in the ferrite slabs, resulting in little wasted power. Thus, the slabs optimize the conversion of the alternating magnetic field power into induced current in the coil 37.

Although in FIG. 7 only two ferrite slabs 58 and 59 are shown, if desired, a single ferrite slab may be used to divert a significant part of the magnetic field which impinges on the metal can and its metallic content, to thereby minimize their heating. Also, if desired, all six sides of the metal can may be surrounded by ferrite slabs. In such an arrangement the metal can 55 can be thought of as being enclosed within a ferrite box. It should be pointed out that the ferrite slab or slabs, by diverting the magnetic field from the metallic content of the metal can 55, i.e., the circuitry therein, prevent the magnetic field from adversely affecting the proper operation of the circuitry. Thus, the ferrite slab or slabs also effectively shield the circuitry from magnetic field interference.

Since the coil 37, as shown in FIG. 7, is wound outside the metal can 55 it may be shielded from conductive currents as hereinbefore described. This may be accomplished with the two coaxial shielding arrangement, as shown in FIG. 6. Furthermore, if desired even with such a shielding arrangement the metal can together with the shielded coil 37 may further be enclosed within shield 30, as shown in FIG. 2, to further reduce the likelihood of the flow of any currents to or from the pacemaker via the body fluid.

The use of one or more ferrite slabs, such as slabs 58 and 59, is not limited for use with a hermetically sealed pacemaker. It can be used with a non-hermetically sealed rechargeable unit. In such a unit block 55 is assumed to represent a block of encapsulating material, such as epoxy, rubber compounds or the like, in which the pacemaker internal components are encapsulated. In such an arrangement the ferrite slab or slabs, in addition to increasing the pick up efficiency of the coil, also serve to divert the magnetic field away from block 55 and thereby minimize the heating of any metallic components encapsulated in it. It should be pointed out that when the ferrite slabs are used with a non-hermetically sealed pacemaker at least the shield 30 should be used to protect the flow of conductive currents to or from the components inside the block 55 of encapsulating matter, which is not completely impervious to body fluid.

Hereinbefore a single coil 37 is shown wound about metal can 35 (see FIG. 5) or about block 55 together with the ferrite slabs 58 and 59, as shown in FIG. 7. The coil 37 was assumed to be the pickup coil for battery recharging. In practice, if the pacemaker is of the type which transmits or receives alternating magnetic signals from the body exterior, one or more coils, serving as transmit and/or receive coils or antennas, may be wound about the ferrite slabs and block 55, in addition to the battery recharging pickup coil. The additional coil or coils may be wound along the same axis as coil 37 or about any other axis.

In FIG. 7, numeral 60 designates the axis about which coil 37 is wound, while numerals 61 and 62 designate axes orthogonal to axis 60 and to each other, and 63 designates a fourth possible axis which is not perpendicular to any of axes 60–62. Clearly, more axes about which different coils can be wound are possible. Since axes 60–62 are orthogonal to one another, coils wound thereabout may be used to maximize or minimize specifically oriented field pick up. For example, an additional coil may be wound about axis 61. Thus, when the external alternating magnetic field is oriented to pass through the pacemaker along axis 60 (as shown) pick up is maximized in coil 37. On the other hand, if the field 57 passes through the pacemaker along axis 61, pick up is maximized in the coil wound about axis 61. Also, it should be pointed out that any coil may be wound about more than one axis. Thus, in the foregoing description the single externally wound coil 37 is intended to represent one or more externally wound coils, which are wound about one or more axes.

The invention as described in connection with FIG. 7 is not intended to be limited to slabs of ferrite. The advantages, realized with ferrite slabs, may be realized with a ferrite coating on the can 55, which may be applied with any known techniques, such as plasma arc spraying, vacuum deposition to mention but two methods. Also, instead of ferrite slabs, several small pieces of ferrite, attached in the form of a series of adjacent tiles, can be used. Also, ferrite powder may be attached to the can 55 by glue, sintering or other known methods. In all of these arrangements the final result is a ferrite layer around at least one side of the pacemaker which extends through one or more externally wound coils.

Instead of ferrite, other materials with high magnetic permeability may be used, e.g., nickel and iron alloys and oxides. These materials can also be applied in different ways, some of which have been mentioned hereinabove while other ways may be obvious to those familiar with the art. It should be pointed out that the materials selected for their high magnetic permeability should also be selected to have high resistance or be slotted in order to minimize their heating. Generally, in most applications the magnetic permeability should be on the order of not less than 100 and preferably 500 and more. However, some advantages may be realized with materials having a magnetic permeability as low as 10. Thus, as used herein, the term "high magnetic permeability" is intended to refer to a magnetic permeability of 10 or more.

Hereinbefore, in the description of FIG. 7 it was assumed that the coil 37 is wound about a block 55 and one or more ferrite slabs. Block 55 was assumed to be either a metal container, which hermetically seals the pacemaker circuitry, or a block of encapsulating material which is not impervious to body saline solution. The invention is not intended to be limited thereto. If desired, the pacemaker circuitry may be mounted on an appropriate support structure, e.g., an integrated circuit board, with the ferrite slab or slabs located on one or more sides thereof and the coil 37 wrapped around the circuitry and the ferrite slab or slabs. The entire assembly, i.e., the coil wrapped around the non-encapsulated circuitry and the ferrite slab or slabs may then be hermetically sealed in an outer hermetic container.

Such an embodiment is shown in FIG. 8. Therein, numeral 70 designates the pacemaker circuitry, such as the battery 14, the pulse generating circuitry 15 and the recharging circuitry 20 (in case of a rechargeable pacemaker), with the coil 37 being shown wound about the circuitry 70 and the ferrite slabs 58 and 59. This entire assembly, designated by 72, is shown enclosed within a hermetic container 74, which hermetically seals the assembly 72 from body saline solution or any gases. If desired, the container 74 may be filled with a non-corroding gas, e.g., helium or nitrogen, or encapsulating matter. Also, the container may be evacuated of any air.

The container 74 may be formed of a biocompatible metal. However, when formed of a metal the metal absorbs a significant portion of the power induced by the external magnetic field which is dissipated as heat in the metal, thereby raising its temperature, which is undesirable. Also, since a significant portion of the induced power is dissipated as heat in the metal container, only a small portion of the total induced power is converted into useful battery charging power. Preferably, the hermetic container 74 is formed of glass and/or ceramic which is impervious to both body saline solution and gases, and exhibits relatively high resistance to corrosion by the body saline solution. The advantages of the glass and/or ceramic hermetic container 74, over one made of metal, is that very little if any heating takes place in the container 74 due to the external magnetic field. Thus, practically all the power induced by the magnetic field enters the container 74. And therein, due to the ferrite slabs 58 and 59, it is diverted from the circuitry 70 and passes through the coil 37 through slabs 58 and 59. Thus, maximum pick up efficiency in coil 37 is achieved.

The use of glass and/or ceramic materials in implantable devices has been studied in the prior art. The results of some of these studies have been published in various publications including Journal of Biomedical Materials Research, published by John Wily & Sons, Inc. In an article by S. D. Davis et al entitled "Biocompatibility of Ceramic Implants in Soft Tissue" appearing in said Journal volume 6, pps. 425–449 (1972) several glass and/or ceramic materials which are potentially useful in implanting devices are presented. Container 74 may be formed from the materials mentioned therein as well as from other glass and/or ceramic materials which are known in the art for their relatively good biocompatibility.

Glass and/or ceramic materials typically exhibit very high electrical resistivity, e.g., $10^{12}$ ohm-cm and higher. Thus, they act as very good electrical insulators. In fabricating container 74 from a glass and/or ceramic material it may be desirable to lower its melting temperature or increase its mechanical strength by including matter, e.g., carbon or lead, which may lower the electrical resistivity of the container-forming material. Preferably, the electrical resistivity should not be less than 1000 ohm-cm. As used hereinafter, the term "implantable type ceramic like material" is intended to include glass and/or ceramic materials with or without matter which may be added to reduce the melting points of such materials and/or increase their mechanical strength, and which exhibit relatively high corrosion to body fluid.

The thickness of the container 74 formed of an implantable type ceramic like material may be on the order of 20 mils or more if the container is self-supporting. On the other hand, it may be only a few mils thick if it is formed on top of supporting matter which acts as a support substrate. It should be pointed out that if desired, the current conductive protective shield, previously describe, may be included within the hermetic container 74 formed of the implantable type ceramic like material. Such a shield will protect the stimulator circuitry from the flow of any currents via body fluid, which may penetrate the container 74 through unexpected cracks therein.

Although particular embodiments of the invention have been described and illustrated herein, it is recognized that modifications and variations may readily occur to those skilled in the art and consequently, it is intended that the claims be interpreted to cover such modifications and equivalents.

The embodiments of the invention in which an exclusive property or privilege is claimed are defined as follows:

1. In an implantable living tissue stimulator of the type comprising a plurality of stimulator circuit means which form the stimulator circuitry and include at least a power source and pulse generating means powered by said power source to provide pulses adapted to be applied to body tissue to be stimulated, with at least some of the stimulator circuit means being exposable to body saline fluid when said stimulator is implanted in a body, the improvement comprising:

current conductive shield means surrounding at least the stimulator circuit means which is exposable to body saline fluid, and connected to a reference potential in said stimulator circuitry for substantially inhibiting the flow of current via body saline fluid to or from said circuit means which are exposable to the body saline fluid, by conducting said current to said reference potential.

2. The improvement as described in claim 1 wherein the stimulator circuit means exposable to said body saline fluid is a coil adapted to have a current induced therein by an alternating magnetic field applied external to the body.

3. The improvement as described in claim 2 wherein said shield means includes at least a first current conductor means surrounding substantially the entire coil exposable to the body saline fluid, with electrically insulating matter between said coil and said first current conductor means, the latter having a first end surrounding a first end of said coil connected to said reference potential and extending to a free floating second end near the second end of said coil.

4. The improvement as described in claim 3 wherein said shield means includes a second current conductor means spaced apart from said first conductor means with electrical insulation matter therebetween, said second conductor means surrounding a portion of said coil from the second end thereof, said second conductor means having a first end which is connected to said reference potential and which surrounds the second end portion of said coil, said second conductor means extending from its first end toward a second free-floating end, with at least a portion of said coil being surrounded by both said first and second conductor means.

5. The improvement as described in claim 1 wherein all of said stimulator circuit means are exposable to body saline fluid, with said current conductive shield means surrounding all of said stimulator circuit means, for substantially inhibiting the flow of currents via the body saline fluid to or from any of the stimulator circuit means.

6. The improvement as described in claim 5 wherein said plurality of stimulator circuit means include at least one coil in which a current is induceable by an alternating magnetic field external to said body.

7. The improvement as described in claim 6 wherein said plurality of stimulator circuit means include recharging means and a pickup coil connected to said recharging means for recharging said power source with the current induced in said pickup coil by the external alternating magnetic field.

8. The improvement as described in claim 7 wherein said power source, said recharging means and said pulse generating means are encapsulated in encapsulating matter which is not impervious to body saline fluid with said pickup coil being wound thereabout, with said shield means surrounding said pickup coil and the encapsulating matter.

9. The improvement as described in claim 8 further including matter means having high magnetic permeability, extending through said pickup coil, for diverting a substantial portion of the magnetic field which passes through said coil from the power source, said recharging means and said pulse generating means which are in said encapsulating matter about which the coil is wound.

10. The improvement as described in claim 1 wherein said plurality of stimulator means include recharging means and a pickup coil in which a current is induced by an external alternating magnetic field for activating said recharging means to recharge said power source, the improvement including a hermetic container for hermetically sealing said recharging means, said power source and said pulse generating means from the body saline fluid, with said pickup coil being external to said hermetic container and connectable therethrough to said recharging means, said pickup coil being surrounded by said shield means.

11. The improvement as described in claim 10 wherein said pickup coil is wound about said hermetic container.

12. The improvement as described in claim 10 wherein said hermetic container is a biocompatible metal, with said pickup coil being wound about it.

13. The improvement as described in claim 12 further including matter means with high magnetic permeability extending through said pickup coil adjacent said hermetic metal container for diverting a substantial portion of the magnetic field which passes through said coil from the hermetic metal container about which the coil is wound.

14. In an implantable living tissue stimulator of the type comprising a plurality of stimulator circuit means which form the stimulator circuitry and include at least a power source, pulse generating means powered by said power source to provide pulses adapted to be applied to tissue to be stimulated, a coil and a circuit connected to said coil and responsive to a current induced in said coil by an alternating magnetic field external to said body, the improvement comprising:
said coil being wound about at least some of said stimulator circuit means; and
matter means of high magnetic permeability extending through the coil for at least diverting a substantial portion of the magnetic field which passes through said coil from the stimulator circuit means about which the coil is wound, the dimension of said matter means along the longitudinal axis of said coil, being not less than the extent of the stimulator circuit means about which said coil is wound, along said longitudinal axis.

15. The improvement as described in claim 14 wherein said circuit to which the coil is connected is a circuit for recharging said power source with the current induced in said coil by the external alternating magnetic field.

16. In an implantable living tissue stimulator of the type comprising a plurality of stimulator circuit means which form the stimulator circuitry and include at least a power source, pulse generating means powered by said power source to provide pulses adapted to be applied to tissue to be stimulated, a coil and a circuit connected to said coil and responsive to a current induced in said coil by an alternating magnetic field external to said body, the improvement comprising:
said coil being wound about at least some of said stimulator circuit means; and
matter means of high magnetic permeability extending through the coil for at least diverting a substantial portion of the magnetic field which passes through said coil from the stimulator circuit means about which the coil is wound, said high magnetic permeability matter means being exposed on at least two sides of the stimulator circuit means about which the coil is wound.

17. The improvement as described in claim 16 wherein said circuit to which the coil is connected is a circuit for recharging said power source with the current induced in said coil by the external alternating magnetic field.

18. The improvement as described in claim 17 further including a hermetic metal container for hermetically sealing all of said stimulating circuit means except said coil from body saline solution with said coil being wound about said hermetic metal container and said matter of high magnetic permeability which extends along at least two sides of said hermetic metal container.

19. The improvement as described in claim 16 further including a hermetic container for hermetically sealing said stimulator circuitry, said coil and said high magnetic permeability matter, said hermetic container being formed of implantable type ceramic like material which is impervious to body saline fluid and gases.

20. The improvement as described in claim 19 wherein said circuit to which the coil is connected is a circuit for recharging said power source with the current induced in said coil by the external alternating magnetic field.

21. The improvement as described in claim 20 wherein said high magnetic permeability matter means extends through said coil on at least two opposite sides of the stimulator circuit means about which said coil is wound.

22. The improvement as described in claim 16 wherein said high magnetic permeability matter means extends through said coil on at least two opposite sides of the stimulator circuit means about which said coil is wound.

23. The improvement as described in claim 16 wherein all of said stimulator circuit means are surrounded by said high magnetic permeability matter means with said coil being wound about said high magnetic permeability matter means.

24. The improvement as described in claim 23 wherein said circuit to which the coil is connected is a circuit for recharging said power source with the current induced in said coil by the external alternating magnetic field.

25. In a living tissue stimulator of the implantable type including a power source and rechargeable means for recharging said power source by responding to an external magnetic field and pulse generating means powered by said power source to provide pulses adapted to be applied to body tissue to be stimulated, the improvement comprising:
current conductive shield means surrounding said stimulator for inhibiting the flow of current from said stimulator or thereto via the body fluid when said stimulator is implanted, said shield means defining a plurality of current conductive members each of which is electrically connected to a reference potential of said power source, said current conductive members being spaced apart from one another whereby any current flowing to or from said stimulator via the body fluid is conducted to said reference potential by at least one of said current conductive members, with any substantially square area on the surface of any of said members being less than the total conductive surface area of said members, by a factor $n$, where $n$ is not less than 100.

* * * * *